United States Patent [19]

Crenshaw et al.

[11] B 4,013,665
[45] Mar. 22, 1977

[54] ANTIVIRAL, SUBSTITUTED 1,3-DIMETHYL-1H-PYRAZOLO(3,4b) QUINOLINES

[75] Inventors: Ronnie Ray Crenshaw, Dewitt; George Michael Luke, Lafayette; Paul Siminoff, Dewitt, all of N.Y.

[73] Assignee: Bristol-Myers Company, New York, N.Y.

[22] Filed: Oct. 1, 1973

[21] Appl. No.: 402,657

[44] Published under the second Trial Voluntary Protest Program on April 6, 1976 as document No. B 402,657.

[52] U.S. Cl. .................. 260/288 CF; 260/244 R; 260/247.1 L; 260/247.5 EP; 260/268 TR; 260/283 S; 260/283 SY; 260/310 R; 424/248.56; 424/250; 424/258
[51] Int. Cl.² ............ C07D 215/46; C07D 215/20
[58] Field of Search ................ 260/288, 288 CF

[56] References Cited
UNITED STATES PATENTS

| | | |
|---|---|---|
| 3,234,142 | 2/1966 | Wolfrum et al. ............ 260/288 R |
| 3,600,393 | 8/1971 | Graeve et al. ............... 260/288 R |
| 3,790,576 | 2/1974 | DeWald ...................... 260/288 CF |

FOREIGN PATENTS OR APPLICATIONS

| | | |
|---|---|---|
| 1,445,719 | 1/1969 | Germany .................... 260/288 CF |
| 1,186,867 | 2/1965 | Germany .................... 260/288 CF |
| 1,152,421 | 8/1963 | Germany .................... 260/288 CF |

OTHER PUBLICATIONS

Wolfrum et al; Chemical Abstracts; vol. 61, Col. 756f; 1963.
Stein et al; Chemical Abstracts; vol. 72, 78941p; 1970.

*Primary Examiner*—Richard J. Gallagher
*Assistant Examiner*—Mary Vaughn
*Attorney, Agent, or Firm*—Robert E. Havranek

[57] ABSTRACT

Compounds of the formula

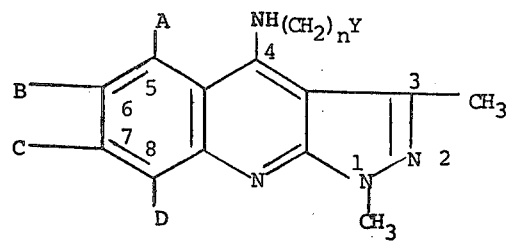

where A is selected from the group consisting of hydrogen, halogen, lower alkoxy, lower alkylthio, hydroxyl, thio, trifluoromethyl, lower diakylaminoalkyl, amino, lower alkylamino and lower dialkylamino, where B is selected from the group consisting of hydrogen, lower alkyl, lower alkoxyl, lower alkylthio, hydroxyl, thio, trifluoromethyl, lower dialkylaminoalkoxyl, amino, lower alkylamino, and lower dialkylamino, where C is selected from the group consisting of hydrogen, halogen, lower alkyl, lower alkoxyl, lower alkylthio, hydroxyl, thio, trifluoromethyl, lower dialkylaminoalkoxy, amino, lower alkylamino and lower dialkylamino, where D is selected from the group consisting of hydrogen, halogen, lower alkyl, lower alkoxy, lower alkylthio, hydroxyl, thio, trifluoromethyl, lower dialkylaminoalkoxyl, amino, lower alkylamino and lower diaklamino, where $n$ is an integer from 2 to 12 inclusive,
and Y is selected from the group consisting of amino, lower alkylamino, lower dialkylamino, and heteroamino wherein the heteroamino group is a 5 or 6 membered saturated ring; or a pharmaceutically acceptable nontoxic salt thereof, exhibit antiviral activity in mammals.

4 Claims, No Drawings

ANTIVIRAL, SUBSTITUTED 1,3-DIMETHYL-1H-PYRAZOLO(3,4b)QUINOLINES

FIELD OF THE INVENTION

This invention relates to certain substituted 1,2-dimethyl-1H-pyrazolo[3,4b]quinolines and particularly to their use as antiviral agents in mammals. In another aspect, this invention relates to a method of preparing certain of such compounds.

DESCRIPTION OF THE PRIOR ART

U.S. Pat. No. 3,600,393 to Graeve et al. describes compounds of the formula

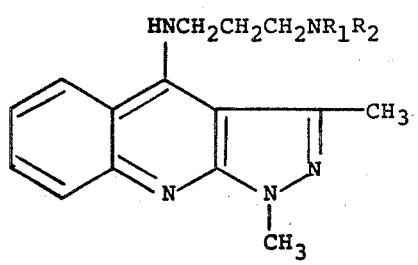

and their pharmaceutically acceptable salts as having hypocholesterolemic and hypolipemic activity. The reaction scheme described therein is useful in preparing the general class of compounds utilized in the instant invention.

Stein et al, *J. Med. Chem.* 13 153 (1970) describes, inter alia, compounds which are 4-nitrogenously substituted -- 7-chloro-1,3-dimethyl-1H-pyrazolo[3,4b]quinolines as having been tested for antimalarial activity.

U.S. Pat. No. 3,234,142 to Wolfrum et al. describes compounds which are substituted 1-methyl-3-alkyl-1H-pyrazolo[3,4b]quinolines, which however do not bear nitrogenous substituents in the 4-position. The reaction scheme described is essentially a reaction scheme which may be utilized to form intermediates used in the preparation of compounds of the instant invention.

DESCRIPTION OF THE INVENTION

It has now been found that compounds corresponding to the formula

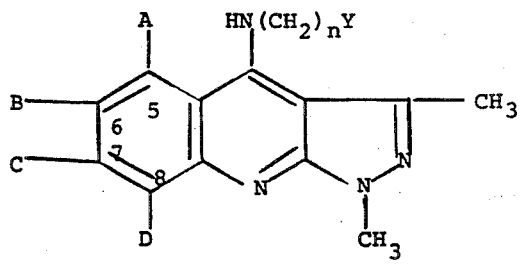

where A is selected from the group consisting of hydrogen, halogen, lower alkoxy, lower alkylthio, hydroxyl, alkylthio, thio, trifluoromethyl, lower dialkylaminoalkoxyl, amino, lower alkylamino and lower dialkylamino, where B is selected from the group consisting of hydrogen, lower alkyl, lower alkoxyl, lower alkylthio, hydroxyl, thio, trifluoromethyl, lower dialkylaminoalkoxyl, amino, lower alkylamino, and lower dialkylamino, where C is selected from the group consisting of hydrogen, halogen, lower alkyl, lower alkoxyl, lower alkylthio, hydroxyl, thio, trifluoromethyl, lower dialkylaminoalkoxy, amino, lower alkylamino and lower dialkylamino, where D is selected from the group consisting of hydrogen, halogen, lower alkyl, lower alkoxy, lower alkylthio, hydroxyl, thio, trifluoromethyl, lower dialkylaminoalkoxyl, amino, lower alkylamino and lower dialkylamino, where n is an integer from 2 to 12 inclusive, and Y is selected from the group consisting of amino, lower alkylamino, lower dialkylamino, and heteroamino wherein the heteroamino group is a 5 or 6 membered saturated ring; or a pharmaceutically acceptable nontoxic salt thereof have antiviral activity in mammals.

The pharmaceutically acceptable nontoxic salts include the organic and inorganic acid addition salts, for example, those prepared from acids such as hydrochloric, sulfuric, sulfonic, tartaric, fumaric, hydrobromic, hydroiodic, glycolic, citric, maleic, phosphoric, succinic, acetic and the like. Such salts are prepared by conventional methods by reacting the free base with the desired acid. The compounds of this invention contain a multiplicity of salt forming groups and any or all of them can be combined with one or more acids to form acid salts.

The term "lower alkyl" as used herein means both straight and branched chain alkyl radicals containing 1 to 8 carbon atoms, for example, methyl, ethyl, propyl, isopropyl, butyl, and the like.

The novel compounds within the scope of this invention corresponding to the formula

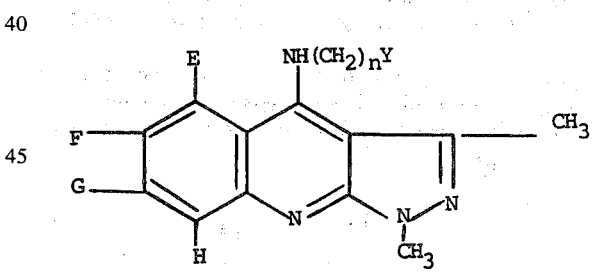

where E is selected from the group consisting of hydrogen, lower alkoxyl, lower alkylthio, hydroxyl, thio, trifluoromethyl, lower dialkylaminoalkoxy, amino, lower alkylamino, and lower dialkylamino, where F is selected from the group consisting of hydrogen, lower alkyl, lower alkoxyl, lower alkylthio, hydroxyl, thio, trifluoromethyl, lower dialkylaminoalkoxy, amino, lower alkylamino, and lower dialkylamino, where G is selected from the group consisting of hydrogen, lower alkyl, lower alkoxyl, lower alkylthio, hydroxyl, thio, trifluoromethyl, lower dialkylaminoalkoxy, amino, lower alkylamino, and lower dialkylamino, where H is selected from the group consisting of hydrogen, lower alkoxyl, lower alkylthio, hydroxyl, thio, trifluoromethyl, lower dialkylaminoalkoxy, amino, lower alkylamino, and lower dialkylamino, where n is an integer from 2 to 12, where Y is selected from the group consisting of amino, lower alkylamino, lower dialkylamino, and heteroamino wherein the heteroamino group is a 5 or 6 membered saturated ring;

and where at least one of A, B, C and D is other than hydrogen.

The preferred antiviral compounds of this invention correspond to the formula where one or two of A, B, C and D are other than hydrogen, where n is an integer from 2 to 6 inclusive, and where Y is selected from the group consisting of dimethylamino, amino, diethylamino, dipropylamino, methylamino, ethylamino, propylamino, tertiary butylamino, and a heteroamino radical selected from the group consisting of

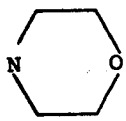 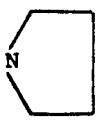  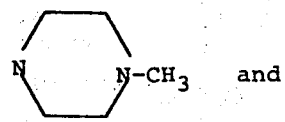 and

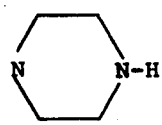

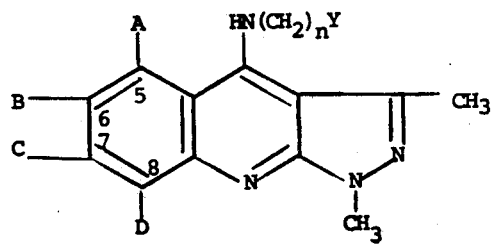

where A is selected from the group hydrogen and lower alkoxy, where B is selected from the group consisting of hydrogen, lower alkyl, lower alkoxyl and lower alkylamino, where C is selected from the group consisting of hydrogen, lower alkyl, lower alkoxyl and halogen, where D is selected from the group consisting of hydrogen and lower alkoxy, The compounds displaying antiviral activity, including novel compounds as described above are prepared by reacting the appropriately substituted 4-chloro-1,3-dimethyl-1H-pyrazolo[3,4b]quinoline with an amine of the formula $H_2N(CH_2)_nY$ where n and Y are defined as above. This reaction is conveniently carried out in the presence of a nonreactive solvent and at elevated temperatures. Suitable solvents include aromatic solvents such as toluene or xylene, or polar solvents such as N,N-dimethylformamide or N,N-dimethylacetamide. Alternatively, an excess of the amine may be used to serve as a solvent. Preferably the reaction is carried out at from about 100°C. to about 200°C. Neither the temperature nor the solvent are critical. The resultant product is readily recoverable by conventional procedures, as for example, exemplified below.

The compounds described herein can generally be prepared according to a reaction scheme described in U.S. Pat. No. 3,600,393 and exemplified below. The reaction scheme is as follows:

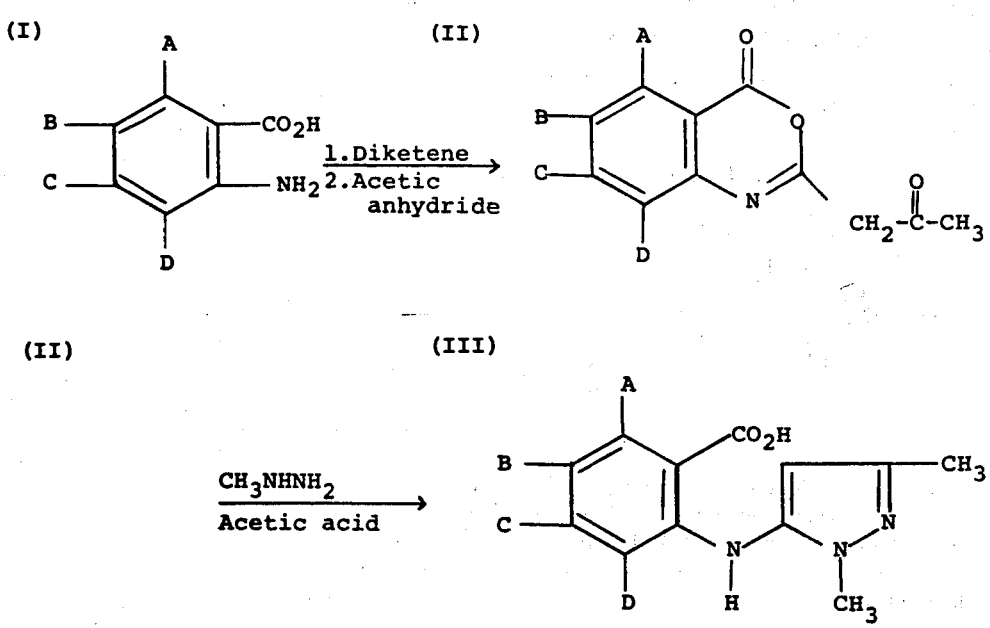

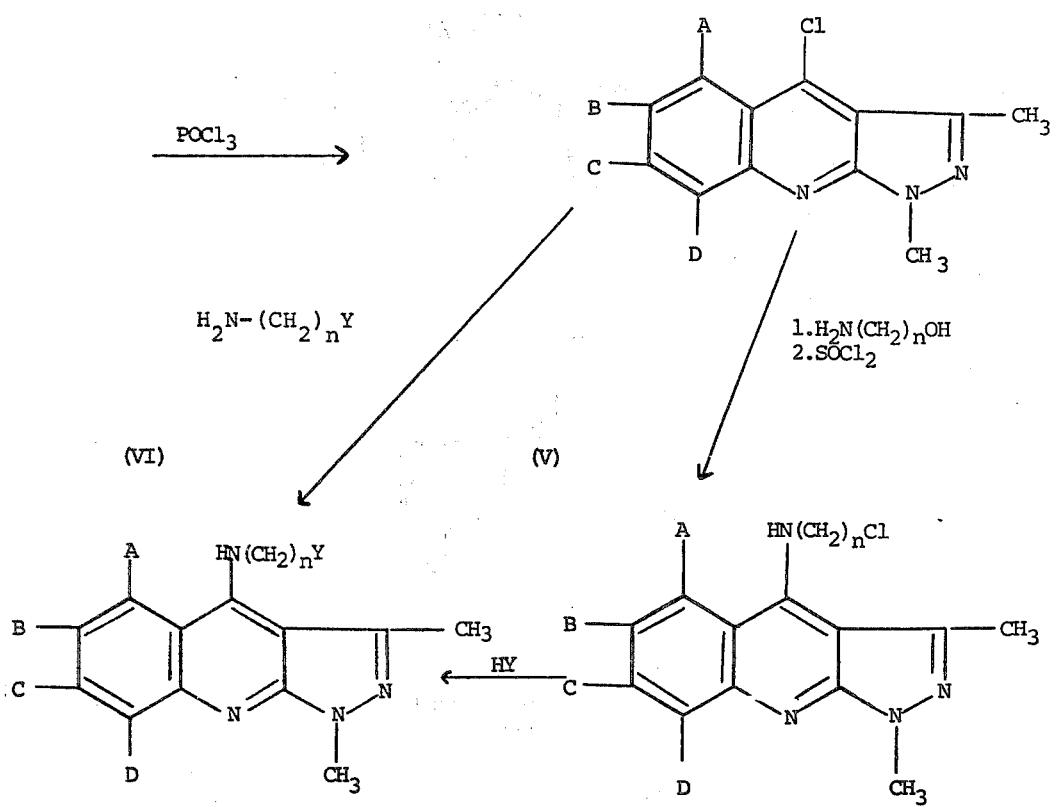
While the above reaction scheme is generally employed to prepare the compounds described above, where B is an amino or substituted amino group the compounds can be prepared according to the following reaction scheme.
The amino group can then, if desired, be substituted by methods known in the art to yield the desired substituted amino group, e.g.,
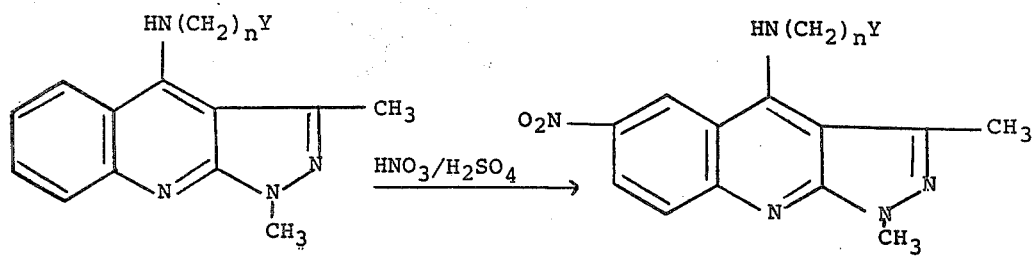
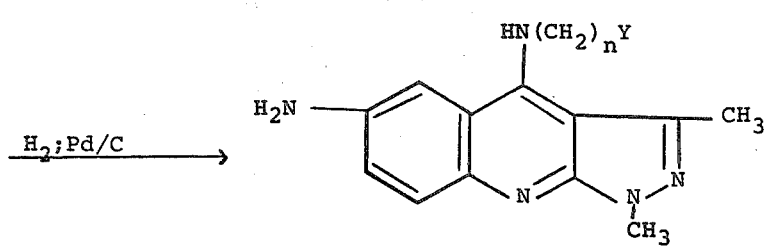

(IX) (X)
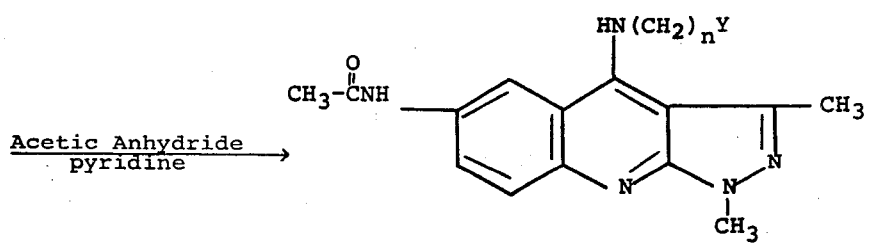
(X) (XI)
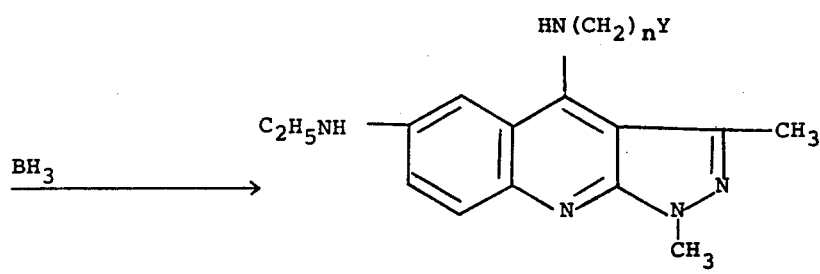
An alternative route for the preparation of intermediate N-(3-methyl-5-pyrazolyl)anthanilic acids, is an Ullmann type reaction according to the following reaction scheme:
(XII)
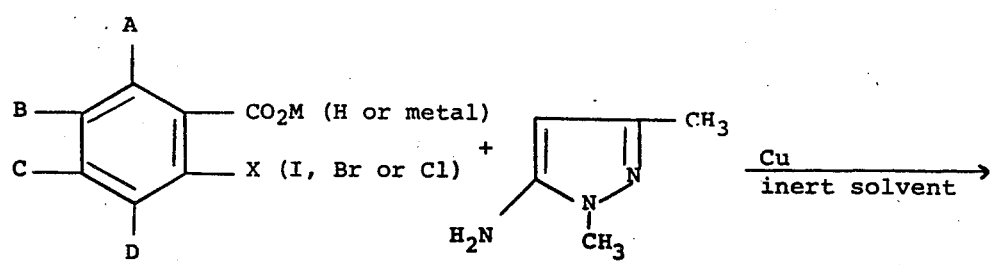
(III)
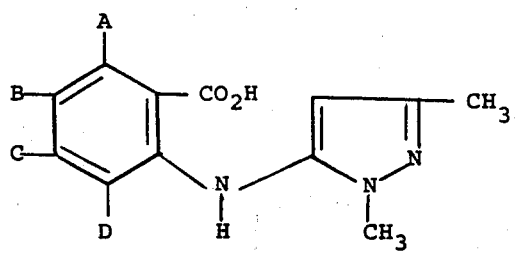

In the above reaction (XII), preferably M is an alkali metal. The catalyst is a copper containing catalyst, examples of which include copper powder, copper-bronze, cupric bromide, cupric oxide, cupric acetate, as well as other copper containing compounds. The reaction is preferably conducted in the presence of an inert solvent, with the application of heat sufficient to promote the reaction. Examples of suitable solvents include dimethyl formamide, n-amyl alcohol, xylene, diethylene glycol dimethyl ether and water.

The invention is further described in conjunction with the following examples, which are to be considered illustrative rather than limiting. All parts and percentages in the examples and throughout the specification are by weight unless otherwise specified. All temperatures are degrees Centigrade unless otherwise stated. In the following examples the formulas set forth are consistent with NMR (Nuclear Magnetic Resonance) and IR (infrared) analysis of the materials.

EXAMPLE 1

2-Acetonyl-7-methyl-4H-3,1-benzoxazin-4-one

A mixture of 4-methylanthranilic acid (25.0 g., 0.17 mole) and diketene (13.95 g., 0.17 mole) in $CCl_4$ (250 ml.) was heated at reflux for 2.5 hours. Acetic anhydride (18.3 g., 0.18 mole) was added and the mixture was stirred under reflux for 16 hours. The mixture then was cooled and the product isolated by filtration; upon recrystallization there was obtained 2-acetonyl-7-methyl-4H-3,1-benzoxazin-4-one (17.4 g., 48 percent), mp 142°–144°C.

Analysis Calculated for $C_{12}H_{11}NO_3$: C, 66.35; H, 5.10; N, 6.45. Found: C, 66.14; H, 5.23; N, 6.39.

EXAMPLE 2A

N-(1,3-Dimethyl-5-pyrazolyl)-4-methylanthranilic acid

The benzoxazinone of Example 1 (15.31 g., 0.071 mole) was added to a solution of methylhydrazine (3.90 g., 0.085 mole) in acetic acid (150 ml.) and the resultant solution was stirred at 80°C. for 2.5 hours. The solvent was removed and the product was recrystallized (acetonitrile) to yield N-(1,3-dimethyl-5-pyrazolyl)-4-methylanthranilic acid (8.59 g., 49 percent), mp 188°–192°C.

Analysis Calculated for $C_{13}H_{15}N_3O_2$: C, 63.66; H, 6.16; N, 17.13. Found: C, 63.47; H, 6.20; N, 17.38.

EXAMPLE 2B

N-(1,3-Dimethyl-5-pyrazolyl)-anthanilic acid

The catalyst employed was prepared by briefly digesting a commercial copper powder (1 micron) in 1 N aqueous hydrochloric acid. The powder was then filtered washed with water and acetone and oven dried.

To a solution of 4.84 grams of potassium carbonate in 18 ml. of water were added in succession 8.0 grams of o-iodobenzoic acid, 3.88 grams of 5-amino-1,3-dimethyl pyrazole and 0.8 gram of the copper catalyst. The mixture was stirred at reflux for 5 hours. There was then added an additional 50 milliliters of water, the mixture being refluxed an additional 30 minutes and then filtered through diatomaceous earth. The filtrate was digested with decolorizing carbon, heated to reflux and filtered. The filtrate was cooled and acidified with 3N aqueous hydrochloric acid to produce N-(1,3-dimethyl-5-pyrazolyl)anthanilic acid, mp 175°–189°C., recrystallized from ethanol to give needles, mp 204°–206° C.

EXAMPLE 3

4-(3-Dimethylaminopropylamino)-1,3,7-trimethyl-1H-pyrazolo[3,4b]quinoline dihydrochloride A mixture of N-(1,3-dimethyl-5-pyrazolyl)-4-methylanthranilic acid (6.47 g., 0.026 mole) and phosphorus oxychloride (65 ml) was stirred at reflux for 3 hours. The cooled mixture was concentrated at 5 mm to a syrup which was poured onto ice. The mixture was basified with 4N NaOH and then was extracted with chloroform. The chloroform extracts were washed, dried and evaporated to yield 4-chloro-1,3,7-trimethyl-1H-pyrazolo[3,4b]quinoline (4.75 g.). The product was treated with 3-dimethylaminopropylamine (50 ml.) and the mixture was stirred at reflux for 12 hours. The mixture was cooled and excess amine was evaporated at 5 mm. The residue was dissolved in chloroform and the resultant solution was wshed in succession with aqueous potassium carbonate, water and brine. Drying ($Na_2SO_4$) and evaporation gave 6.86 g. Dissolution in 1-propanol and treatment with 2 equivalents of aqueous 1N hydrochloride acid yielded, after evaporation, 4-(3-dimethylaminopropylamino)-1,3,7-trimethyl-1H-pyrazolo[3,4b]quinoline dihydrochloride; recrystallization (aqueous ethanol) gave mp 290°–293°C. (dec.).

Analysis Calculated for $C_{18}H_{25}N_5 \cdot 2HCl$: C, 56.25; H, 7.08; N, 18.22. Found: C, 56.45; H, 7.12; N, 18.24.

EXAMPLE 4

1,3-Dimethyl-4-(4-dimethylaminobutylamino)-1H-pyrazolo[3,4b]quinoline Dihydrochloride A mixture of 4-chloro-1,3-dimethyl-1H-pyrazolo[3,4b]quinoline (4.63 g., 0.02 mole), potassium carbonate (2.76 g., 0.02 mole), and 4-dimethylaminobutylamine (2.23 g., 0.02 mole) in dimethylformamide (DMF) (60 ml.) was stirred at 130° for 16 hours. The solvent was removed at 5 mm and the residue was partitioned between water and chloroform. The organic phase was separated, washed with water, dried and evaporated to leave an oil (6.02 g., 97 percent). The dihydrochloride salt was prepared as described above; recrystallization (ethanol) yielded 1,3-dimethyl-4-(4-dimethylaminobutylamino)-1H-pyrazolo[3,4b]quinoline dihydrochloride mp 294°C. (dec.).

Analysis Calculated for $C_{18}H_{25}N_5 \cdot 2HCl$: C, 56.25; H, 7.08; N, 18.22. Found: C, 55.68; H, 6.88; N, 18.32.

EXAMPLE 5

1,3-Dimethyl-4-(3-hydroxypropylamino)-1H-pyrazolo[3,4b]quinoline hydrochloride

A mixture of 4-chloro-1,3-dimethyl-1H-pyrazolo[3,4b]quinoline (13.89 g., 0.06 mole), potassium carbonate (8.28 g., 0.06 mole), and 3-amino-1-propanol (4.95., 0.07 mole) in DMF (180 ml.) was stirred at 130° for 15 hours. Removal of the DMF and workup as described in Example 4 gave 11.92 g. (74 percent) of 1,3-dimethyl-4-(3-hydroxypropylamino)-1H-pyrazolo[3,4b]quinoline, mp 153.5°–155°C. The hydrochloride salt was prepared as described above; mp 252.2°–254.5°C.

Analysis Calculated for $C_{15}H_{18}N_4O·HCl$: C, 58.75; H, 6.25; N, 18.27; Cl, 11.56. Found: C, 59.16; H, 6.26; N, 18.54; Cl, 11.59.

EXAMPLE 6

1,3-Dimethyl-4-(3-chloropropylamino)-1H-pyrazolo[3,4b]quinoline hydrochloride A solution of the hydroxy compound of Example 5 (11.50 g., 0.038 mole) and thionyl chloride (110 ml.) was heated at 60° for 2 hours. Evaporation yielded 4-(3-chloropropylamino)-1,3-dimethyl-1H-pyrazolo[3,4b]quinoline hydrochloride; mp 210°–214° after recrystallization (absolute ethanol).

Analysis Calculated for $C_{15}H_{17}ClN_4·HCl$: C, 55.40; H, 5.58; N, 17.23 Found C, 55.14; H, 5.61; N, 17.44.

EXAMPLE 7

1,3-Dimethyl-4-[3-(N'-methylpiperazino)-propylamino]-1H-pyrazolo[3,4b]quinoline dihydrochloride A mixture of 4-(3-chloropropylamino)-1,3-dimethyl-1H-pyrazolo[3,4b]quinoline hydrochloride (4.63 g., 0.02 mole), N-($\mu$-aminopropyl)-N'-methylpiperazine (3.15 g., 0.02 mole), and potassium carbonate (2.76 g., 0.02 mole) in DMF (60 ml.) was stirred at 130°C. for 18 hours. The solvent was removed at 5 mm, and the residue was dissolved in chloroform. The solution was washed with water, dried and evaporated to leave 5.24 g. (75 percent). Treatment with two equivalents of hydrochloric acid yielded 1,3-dimethyl-4-[3-(N'-methylpiperazino)propylamino]-1H-pyrazolo[3,4b]quinoline dihydrochloride; mp 266°–270°C. (dec.) after recrystallization (ethanol).

Analysis Calculated for $C_{20}H_{28}N_6·2HCl$: C, 56.47; H, 7.11; N, 19.76. Found: C, 55.90; H, 6.80; N, 19.91.

EXAMPLE 8

1,3-Dimethyl-4-(3-dimethylaminopropylamino)-6-nitro-1H-pyrazolo[3,4b]quinoline A mixture of 70 percent nitric acid (1.2 ml.) and 95 percent sulfuric acid (13.6 ml.) was added dropwise over 30 minutes to a solution at 5°C. of 1,3-dimethyl-4-(3-dimethylaminopropylamino)-1H-pyrazolo[3,4b]quinoline (4.91 g., 0.017 mole) in nitromethane (30 ml.). After the addition, the mixture was stirred at 10°–20°C. for 2 hours, and then was diluted with cold water and neutralized with ammonium hydroxide. The product 1,3-dimethyl-4-(3-dimethylaminopropylamino)-6-nitro-1H-pyrazolo[3,4b]quinoline was isolated by extraction into chloroform and worked up in the usual manner; yield, 4.61 g. (82 percent), mp 189°–192°C.; dihydrochloride salt, mp 262°–264°C. (dec.).

Analysis Calculated for $C_{17}H_{22}N_6O_2·2HCl$: C, 49.17; H, 5.83; N, 20.23. Found: C, 48.54; H, 6.02; N, 20.08.

EXAMPLE 9

6-Amino-1,3-dimethyl-4-(3-dimethylaminopropylamino)-1H-pyrazolo[3,4b]quinoline Dihydrochloride The nitro compound of Example 8 (4.00 g., 0.012 mole) suspended in ethanol (100 ml.) containing 5 percent Pd/C (0.4 g.) was shaken under hydrogen at an initial pressure of 50 psi for 2.5 hours. The catalyst was removed by filtration and the solvent was evaporated to leave the 6-amino-1,3-dimethyl-4-(3-dimethylaminopropylamino)-1H-pyrazolo[3,4b]quinoline dihydrochloride. It is necessary to store the compound under nitrogen because it rapidly darkens upon exposure to air. The compound was converted to the dihydrochloride salt in the usual manner and recrystallized (ethanol); mp 305°C. (dec.).

Analysis Calculated for $C_{17}H_{24}N_6·2HCl$: C, 52.99; H, 6.80; N, 21.81. Found: C, 51.19; H, 7.21; N, 21.07.

EXAMPLE 10

6-Acetamido-1,3-dimethyl-4-(3-dimethylaminopropylamino)-1H-pyrazolo[3,4b]quinoline The amine of Example 9 (1.85 g., 0.0059 mole) in pyridine (30 ml.) was treated with acetic anhydride (0.61 g., 0.0059 mole) and the solution was stirred at 28°C. for 16 hours. The solution was poured onto ice-water, treated with 4N aqueous NaOH and extracted with chloroform. Evaporation of the dried organic phase yielded 6-acetamido-1,3-dimethyl-4-(3-dimethylaminopropylamino)-1H-pyrazolo[3,4b]quinoline; recrystallization from water gave mp 64°–76°C. (hydrated).

Analysis Calculated for $C_{19}H_{26}N_6O$: C, 64.38; H, 7.39; N, 23.71. Found (corrected for 3.76% water of hydration): C, 64.52; H, 7.12; N, 24.08.

EXAMPLE 11

1,3-Dimethyl-4-(3-dimethylaminopropylamino)-6-ethylamino-1H-pyrazolo[3,4b]quinoline The acetamido compound of Example 10 (1.34 g., 0.0038 mole) in tetrahydrofuran (THF) (10 ml.) was added over a 30 minute period to 8.86 ml. of 1 molar borane in THF at 5°–10°C. After the addition, the solution was refluxed for 1.5 hours, then cooled and treated with 4N hydrochloric acid (6 ml.). The THF was evaporated and the aqueous was neutralized with 4N sodium hydroxide. Extraction with chloroform and workup in the usual manner yielded 1,3-dimethyl-4-(3-dimethylaminopropylamino)-6-ethylamino-1H-pyrazolo[3,4b]quinoline; treatment with three equivalents of hydrochloric acid and subsequent recrystallizations from ethanol gave an equimolar mixture of di and trihydrochloride salts; mp 210°–214°C. (dec.). Analysis Calculated for $C_{19}H_{28}N_6·2.5HCl$: C, 52.87; H, 7.12; N, 19.47; Cl, 20.53. Found: C, 53.23; H, 6.63; N, 19.80; Cl, 20.86.

EXAMPLE 12

4-(3-Dimethylaminopropylamino)-1,3,6,7-tetramethyl-1H-pyrazolo[3,4b]quinoline dihydrochloride N-(1,3-dimethyl-5-pyrazolyl)-4,5-dimethylanthranilic acid (2.85 g., 0.011 mole) and phosphorus oxychloride (60 ml.) was stirred at reflux for 1.5 hours. The $POCl_3$ was then evaporated and the residue cooled, during excess 3-dimethylaminopropylamine (about 60 ml.). The reaction mixture then was refluxed for 16 hours. The reaction then was cooled and evaporated.

The residue was dissolved in chloroform and the resultant solution was washed in succession with aqueous potassium carbonate, water and brine, dried with $Na_2SO_4$ and evaporated to yield 3.34 g. of yellow solid (94 percent yield). Dissolution in 1-propanol and heating with 2 equivalents of aqueous 1N hydrochloric acid yield, after filtering and cooling to 4°C. there was recovered 4-(3-Dimethylaminopropylamino)-1,3,6,7-tetramethyl-1H-pyrazolo[3,4b]quinoline dihydrochloride, white crystals, mp greater than 300°C.

Analysis Calculated for $C_{19}H_{27}N_5.2HCl$: C, 57.28; H, 7.34; N, 17.58. Found: C, 56.88; H, 7.12; N, 17.19

EXAMPLE 13

1,3-Dimethyl-4-(3-dimethylaminopropylamino)-6-methoxy-1H-pyrazolo[3,4b]quinoline dihydrochloride 4-chloro-1,3-dimethyl-6-methoxy-1H-pyrazolo[3,4b]quinoline 0.825 g. (0.00316 mol) prepared as above from N-(1,3-dimethyl-pyrazolyl)-5-methoxyanthranilic acid, was mixed with about 10 ml. of 3-dimethylaminopropylamine and refluxed for 16 hours. The product was cooled and extracted as above, isolated and treated in 1-propanol with 2 equivalents in aqueous 1N HCl and then evaporated. The solid was dissolved in hot ethanol then cooled to 4° and stored until needle like crystals formed. Filtered and the crystals were repeatedly washed with cold ethanol. Crystals were dried under vacuum M.P. 281°–282°C. (dec.).

Analysis Calculated for $C_{18}H_{25}N_5O.2HCl$: C, 54.00; H, 6.80; N, 17.49. Found: C, 53.87; H, 6.49; N, 17.51.

EXAMPLE 14

1,3-Dimethyl-4-(3-dimethylaminopropylamino-7-ethyl-1H-pyrazolo[3,4b]quinoline dihydrochloride A mixture of N-(1,3-dimethyl-5-pyrazolyl)-4-ethylanthranilic acid (5.00 g., .0193 mol) and phosphorus oxychloride (50 ml.) was stirred at reflux for 2 hours. Excess $POCl_3$ was then removed at reduced pressure and the residue heated with 3-dimethylaminopropylamine (60 ml) at 130°C. for 16 hours.

The excess amine was then removed at reduced pressure and the oily residue taken up in chloroform, washed with aqueous sodium carbonate, water and brine, dried over $Na_2SO_4$ and the chloroform evaporated to yield 6.98 g. of a yellow brown oil.

The dihydrochloride salt was prepared, as above, using 4.0N HCl. The crude solid salt was washed with acetone and recrystallized from N-propanol, then isopropanol to yield 5.25 g. of a white solid, 1,3-dimethyl-4-(1,3-dimethylaminopropylamino)-7-ethyl-1H-pyrazolo[3,4b]quinoline dihydrochloride, M.P. 248°–251°C. (dec.).

Analysis calculated for $C_{19}H_{27}N_5.2HCl$: C, 57.29; H, 7.34; N, 17.58. Found: C, 57.20; H, 7.61; N, 17.62.

EXAMPLE 15

1,3-Dimethyl-4-(3-dimethylaminopropylamino)-6,7-dimethoxy-1H-pyrazolo[3,4b]quinoline dihydrochloride A mixture of N-(1,3-dimethyl-5-pyrazolyl)-4,5-dimethoxyanthranilic acid (7.0 g., .0241 mol) and phosphorus oxychloride (100 ml.) was stirred at reflux for 3 hours, cooled and the excess $POCl_3$ removed under reduced pressure. The resultant solid was heated with 3-dimethylaminopropylamine (100 ml.) at 174°C. for 18 hours.

The cooled reaction mixture was partitioned between a large volume of aqueous sodium carbonate and chloroform. The organic layer then was washed with water and brine, dried over $Na_2SO_4$ and evaporated to yield 5.0 g. of semicrystalline material which was rubbed under cold ether and filtered. The filtrate was concentrated to remove solvent yielding 3.35 g. of a viscous oil which was placed on 75 g. of alumina on a column and eluted with 500 ml. 95/5, ether/ethanol. The eluant was concentrated to dryness yielding 2.10 g. of an oil, which partially crystallized on standing. This material was rubbed under a minimum amount of cold ether and filtered to yield 753 mg. of sticky solid. The dihydrochloride salt was prepared as previously described; M.P. 259°–261°C. (dec.).

Analysis Calculated for $C_{19}H_{27}N_5O_2.2HCl$: C, 53.03; H, 6.79; N, 16.27. Found: C, 53.55; H, 6.66; N, 15.90.

EXAMPLE 16

1,3-Dimethyl-4-(3-dimethylaminopropylamino)-7-chloro-1H-pyrazolo[3,4b]quinoline dihydrochloride In the manner of the previous Examples N-(1,3-dimethyl-5-pyrazolyl)-4-chloroanthranilic acid was reacted with $POCl_3$ followed by 3-dimethylaminopropylamine. The product was dissolved in chloroform, washed and isolated as previously described. The dihydrochloride salt was formed, washed with acetone and recrystallized from hot aqueous ethanol to yield 4-(3-dimethylaminopropylamino)-1,3-dimethyl-7-chloro-1H-pyrazolo[3,4b]quinoline dihydrochloride.

Analysis Calculated for $C_{17}H_{22}ClN_5.2HCl$: C, 50.57; H, 5.96; N, 17.30. Found: C, 50.70; H, 6.17; N, 17.71.

EXAMPLE 17

1,3-Dimethyl-4-(3-piperazinopropylamino)-1H-pyrazolo[3,4b]quinoline trihydrochloride 4-(3-chloropropylamino)-1,3-dimethyl-1H-pyrazolo[3,4b]quinoline (3.00 g., 0.00923 mol) was reacted with excess piperazine under nitrogen at 148°C. for 16 hours. The cooled pasty reaction product was partitioned between water and chloroform. The organic phase was washed with water and brine, dried and evaporated. The product was washed with toluene, filtered and the filtrate concentrated to yield 1.52 g. of yellow-brown gum. A trihydrochloride was prepared as previously described. The crude salt was washed with acetone and filtered to yield 1.18 g. of yellow solid which was recrystallized from aqueous ethanol to yield 850 mg., 1,3-dimethyl-4-(3-piperazinopropylamino)-1H-pyrazolo[3,4b]quinoline trihydrochloride, M.P. 282°–286°C. (dec.).

Analysis Calculated for $C_{19}H_{26}N_6.3HCl$: C, 50.97; H, 6.53; N, 18.77. Found: C, 51.25; H, 6.03; N, 19.00.

EXAMPLE 18

1,3-Dimethyl-4-(3-Isopropylaminopropylamino)-1H-pyrazolo[3,4b]quinoline dihydrochloride 4-(3-chloropropylamino)-1,3-dimethyl-1H-pyrazolo[3,4b]quinoline (3.50 g., 0.01075 mol) was reacted with isopropylamine (40 ml.) in a pressure vessel at 100°C. for 16 hours. The cooled reaction product was dissolved in chloroform and washed with aqueous sodium carbonate; water and brine, dried and evaporated. The dihydrochloride salt was prepared from the free base and aqueous 4N HCl. The crude salt was washed with acetone and recrystallized from aqueous ethanol to recover 1.75 g. 1,3-dimethyl-4-(3-isopropylaminopropylamino)-1H-pyrazolo[3,4b]quinoline dihydrochloride; M.P. greater than 300°C.

Analysis Calculated for $C_{18}H_{25}N_5 \cdot 2HCl$: C, 56.26; H, 7.08; N, 18.22. Found: C, 56.26; H, 6.95; N, 18.32.

EXAMPLE 19

1,3-Dimethyl-4-(3-tert-butylaminopropylamino)-1H-pyrazolo[3,4b]quinoline dihydrochloride In the manner of Example 18, replacing isopropylamine with tert-butylamine, there was prepared 4-(3-tert-butylaminopropylamino)-1,3-dimethyl-1H-pyrazolo[3,4b]quinoline dihydrochloride.

Analysis Calculated for $C_{19}H_{27}N_5 \cdot 2HCl$: 57.29; H, 7.34; N, 17,58. Found: C, 57.11; H, 7.31; N, 18.04.

EXAMPLE 20

4-(3-Dimethylaminopropylamino)-1,3,6-trimethyl-1H-pyrazolo[3,4b]quinoline dichloride A mixture of N(1,3-dimethyl-5-pyrazolyl)-5-methyanthranilic acid (3.70 g., 0.0151 mol) and phosphorus oxychloride (65 ml.) was stirred at reflux for 3 hours. After removal of excess $POCl_3$ there was added an excess of 3-dimethylaminopropylamine and the mixture refluxed for 16 hours. The excess amine was then removed and the product extracted with chloroform, washed and isolated, as described above; to yield 4.59 g. of a yellow solid. The product dissolved in 1-propanol was treated with two equivalents of 1N aqueous HCl to form the dihydrochloride which was isolated by evaporation. The product was recrystallized from ethanol to yield 4.06 g. of a white solid 4-(3-dimethylaminopropylamino)-1,3,6-trimethyl-1H-pyrazolo[3,4b]quinoline dihydrochloride; M.P. 274°C. (dec).

Analysis Calculated for $C_{18}H_{25}N_5 \cdot 2HCl$: C, 56.25; H, 7.08; N, 18.22. Found: C, 57.75; H, 6.62; N, 18.48.

In the manner of the general reaction schemes set forth and the preceding examples there were prepared the following compounds:

EXAMPLE 21

1,3-Dimethyl-4-(3-dimethylaminopropylamino)-5-methoxy-1H-pyrazolo[3,4b]quinoline dihydrochloride Recrystallized from aqueous ethanol, M.P. 278°C. (dec).

Analysis Calculated for $C_{18}H_{25}N_5O \cdot 2HCl$: C, 54.00; H, 6.80; N, 17.49. Found: C, 54.17; H, 6.72; N, 17.43.

EXAMPLE 22

1,3-Dimethyl-4-(2-dimethylaminoethylamino)-1H-pyrazolo[3,4b]quinoline dihydrochloride Recrystallization from aqueous ethanol, M.P. greater than 300°C.

Analysis Calculated for $C_{16}H_{21}N_5 \cdot 2HCl$: C, 53.94; H, 6.51; N, 19.66. Found: C, 54.10; H, 6.38; N, 19,98.

EXAMPLE 23

1,3-Dimethyl-4-(5-dimethylaminopentylamino)-1H-pyrazolo[3,4b]quinoline dihydrochloride Recrystallized from ethanol, M.P. 269°–271°C. (dec.).

Analysis Calculated for $C_{19}H_{27}N_5 \cdot 2HCl$: C, 57.28; H, 7.38; N, 17.58. Found: C, 57.09; H, 7.05; N, 17.68.

EXAMPLE 24

1,3-Dimethyl-4-(6-dimethylaminohexylamino)-1H-pyrazolo[3,4b]quinoline dihydrochloride Recrystallized from ethanol, M.P. 215°–219°C (dec).

Analysis Calculated for $C_{20}H_{29}N_5 \cdot 2HCl$: C, 58.25; H, 7.58; N, 16.99. Found: C, 58.32; H, 7.74; N, 16.83.

EXAMPLE 25

1,3-Dimethyl-4-(3-methylaminopropylamino)-1H-pyrazolo[3,4b]quinoline dihydrochloride Recrystallized from ethanol, M.P. 307°–309°C (dec).

Analysis Calculated for $C_{16}H_{29}N_5 \cdot 2HCl$: C, 53.94; H, 6.51; N, 19.66. Found: C, 54.20; H, 6.58; N, 19.70.

EXAMPLE 26

1,3-Dimethyl-4-(3-aminopropylamino)-1H-pyrazolo[3,4b]quinoline dihydrochloride Recrystallized from ethanol, M.P. 311°–214°C. (dec.).

Analysis Calculated for $C_{15}H_{19}N_5 \cdot 2HCl$: C, 52.64; H, 6.19; N, 20.46. Found: C, 52.45; H, 6.33; N, 20.60.

EXAMPLE 27

1,3-Dimethyl-4-(3-dimethylaminopropylamino)-8-methoxy-1H-pyrazolo[3,4b]quinoline dihydrochloride Recrystallized from ethanol, M.P. 261.5°–263°C. (dec).

Analysis Calculated for $C_{18}H_{25}N_5O \cdot 2HCl$: C, 54.00; H, 6.80; N, 17.49. Found: C, 54.26; H, 7.03; N, 17.90.

EXAMPLE 28

1,3-Dimethyl-4-(3-dimethylaminopropylamino)-7-methoxy-1H-pyrazolo[3,4b]quinoline dihydrochloride Recrystallized from ethanol, M.P. 261°–263°C. C, 54.00; H, 6.80; N, 17.49. Found: C, 53.85; H, 7.19; N, 17.63.

EXAMPLE 29

1,3-Dimethyl-4-(3-dimethylaminopropylamino)-5,7-dimethoxy-1H-pyrazolo[3,4b]quinoline dihydrochloride Recrystallized from ethanol, M.P. 285°C. (dec.).

Analysis Calculated for $C_{19}H_{27}N_5O_2 \cdot 2HCl$: C, 53.03; H, 6.79; N, 16.27. Found: C, 52.96; H, 6.93; N, 16.44.

The compounds of this invention demonstrate antiviral activity making them useful as antiviral agents in mammals. The compounds of the instant invention have shown interferon-eliciting activity when administered to mice either p.o. or i.p.

The compounds of Examples 3 and 20 have been shown effective against tail lesions induced by vaccinia virus in mice (50mg./kg. orally) following the procedure of Boyle et al, "Antimicrobial Agents and Chemotherapy" (1966):536–539 (1967). Specifically, the compound was administered to mice at any time from 6–24 hours prior to challenge with virus. Vaccinia virus, IHD strain, was introduced into the animals via the tail vein at a dose sufficient to produce 20 to 30 tail lesions per mouse. Lesions were enumerated after 7 days. A reduction in the lesion score of greater than 50 percent was considered significant.

The interferon-eliciting tests summarized in the following table were performed as follows: various concentrations of the compounds, as indicated were administered to 15 gram female CD-1 mice (Charles River Breeding Laboratories) by oral or intraperitoneal route. Approximately 16–18 hours later, the mice were exsanguinated, serum collected and tested on mouse L cells for ability to prevent subsequent infection by vesicular stomatitis virus or mouse picornavirus GD-7. See Siminoff et al, "Antimicrobial Agents and Chemotherapy" 3:742–743 (1973) and Baron et al, "Science" 141:1061–1063 (1963). In the following table, a "+" indicates activity, a "±" low activity and a "−" lack of significant activity. T indicates toxicity.

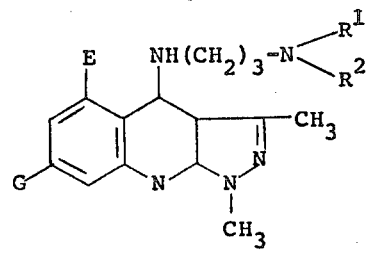

wherein E is hydrogen or lower alkoxy of 1 to 3 carbon atoms, G is lower alkyl or lower alkoxy of 1 to 3 carbon atoms, $R^1$ and $R^2$ are alike or different and each is

|  | Interferon Activity | | | |
|---|---|---|---|---|
|  | p.o. (Mg/Kg) | | i.p. (Mg/Kg) | |
|  | 400 | 100 | 300 | 100 |
| 4-(3-dimethylaminopropylamino)-1,3,7-trimethyl-1H-pyrazolo[3,4b]quinoline dihydrochloride (Ex. 3) | + | + | T | + |
| 4-(3-dimethylaminopropylamino)-1,3,6-trimethyl-1H-pyrazolo[3,4b]quinoline dihydrochloride (Ex. 20) | + | + | T | + |
| 4-(3-dimethylaminopropylamino)-1,3,6,7-tetramethyl-1H-pyrazolo[3,4b] quinoline dihydrochloride (Ex. 12) |  |  | + | + |
| 1,3-dimethyl-4-(3-dimethylaminopropylamino)-6,7-dimethoxy-1H-pyrazolo[3,4b]quinoline dihydrochloride (Ex. 15) |  |  | + | + |
| 1,3-dimethyl-4-(3-dimethylaminopropylamino)-5,7-dimethoxy-1H-pyrazolo[3,4b]quinoline dihydrochloride (Ex. 29) |  |  | + | + |
| 1,3-dimethyl-4-(3-dimethylaminopropylamino)-6-methoxy-1H-pyrazolo[3,4b] quinoline dihydrochloride (Ex. 13) | + | ± | + | ± |
| 1,3-dimethyl-4-(3-dimethylaminopropylamino)-5-methoxy-1H-pyrazolo[3,4b] quinoline dihydrochloride (Ex. 21) | + | + | + | + |
| 1,3-dimethyl-4-(3-dimethylaminopropylamino)-7-methoxy-1H-pyrazolo[3,4b] quinoline dihydrochloride (Ex. 28) | ± | + | + | + |
| 1,3-dimethyl-4-(3-dimethylaminopropylamino)-8-methoxy-1H-pyrazolo[3,4b] quinoline dihydrochloride (Ex. 27) |  | + | + | + |
| 1,3-dimethyl-4-(3-dimethylaminopropylamino)-7-chloro-1H-pyrazolo[3,4b] quinoline dihydrochloride (Ex. 16) |  |  | + | + |
| 1,3-dimethyl-4-(3-dimethylaminopropylamino)-6-ethylamino-1H-pyrazolo[3,4b]quinoline-tri-hydrochloride (Ex. 11) |  |  | + | + |
| 1,3-dimethyl-4-(2-dimethylaminoethylamino)-1H-pyrazolo[3,4b]quinoline dihydrochloride (Ex. 22) | ± | − |  |  |
| 1,3-dimethyl-4-(4-dimethylaminobutylamino)-1H-pyrazolo[3,4b]quinoline dihydrochloride (Ex. 4) | + | − |  |  |
| 1,3-dimethyl-4-(5-dimethylaminopentylamino)-1H-pyrazolo[3,4b]quinoline dihydrochloride (Ex. 23) | + | ± | + | ± |
| 1,3-dimethyl-4-(6-dimethylaminohexylamino-1H-pyrazolo[3,4b]quinoline dihydrochloride (Ex. 24) | + | − |  |  |
| 1,3-dimethyl-4-(3-methylaminopropylamino)-1H-pyrazolo[3,4b]quinoline dihydrochloride (Ex. 25) | + | − | + | − |
| 1,3-dimethyl-4-(3-N-methylpiperazino)-1H-pyrazolo[3,4b]quinoline dihydrochloride (Ex. 7) | + | ± | + | ± |
| 1,3-dimethyl-4-(3-aminopropylamino)-1H-pyrazolo[3,4b]quinoline dihydrochloride (Ex. 26) | + | − | + | − |
| 1,3-dimethyl-4-(3-piperazinopropylamino)-1H-pyrazolo[3,4b]quinoline trihydrochloride (Ex. 17) |  |  | + | ± |
| 1,3-dimethyl-4-(3-isopropylaminopropylamino)-1H-pyrazolo[3,4b]quinoline dihydrochloride (Ex. 18) |  |  | + | − |
| 1,3-dimethyl-4-(3-t-butylaminopropylamino)-1H-pyrazolo[3,4b]quinoline dihydrochloride (Ex. 19) |  |  | + | − |
| 1,3-dimethyl-4-(3-dimethylaminopropylamino)-7-ethyl-1H-pyrazolo[3,4b] quinoline dihydrochloride (Ex. 14) |  |  | T | + |
| 1,3-dimethyl-4-(3-dimethylaminopropylamino)-1H-pyrazolo[3,4b]quinoline dihydrochloride | + | − | + | ± |
| 4-(3-dimethylaminopropylamino)-1,3,7,8-tetramethyl-1H-pyrazolo[3,4b] quinoline dihydrochloride | + | ± |  |  |
| 4-(3-dimethylaminopropylamino)-1,3,6,8-tetramethyl-1H-pyrazolo[3,4b] quinoline dihydrochloride | + | − |  |  |

The compounds of the instant invention are capable of eliciting interferon synthesis and release, thereby making them effective as prophylatic and therapeutic agents in the prevention and/or treatment of viral infections in mammals, including man.

The compounds are administered in man at a dosage in the range of 50–2000 mg three to four times a day, dependent upon the weight of the subject and the route of administration.

We claim:
1. A compound corresponding to the formula lower alkyl of 1 to 5 carbon atoms; or a pharmaceutically acceptable salt thereof.

2. A compound as in claim 1, which is 4-(3-dimethylaminopropylamino)-1,3,7-trimethyl-1H-pyrazolo[3,4b]quinoline; or a pharmaceutically acceptable salt thereof.

3. A compound as in claim 1, which is 4-(3-dimethylaminopropylamino)-1,3,7-trimethyl-1H-pyrazolo[3,4b]quinoline dihydrochloride.

4. A compound, as in claim 1, which is 1,3-dimethyl-4-(3-dimethylaminopropylamino)-5,7-dimethoxy-1H-pyrazolo[3,4b]quinoline; or a pharmaceutically acceptable salt thereof.

* * * * *

UNITED STATES PATENT AND TRADEMARK OFFICE
CERTIFICATE OF CORRECTION

PATENT NO. : 4,013,665
DATED : March 22, 1977
INVENTOR(S) : R. R. Crenshaw, G. M. Luke and P. Siminoff It is certified that error appears in the above-identified patent and that said Letters Patent are hereby corrected as shown below:

In Claim 1, the structural formula should read

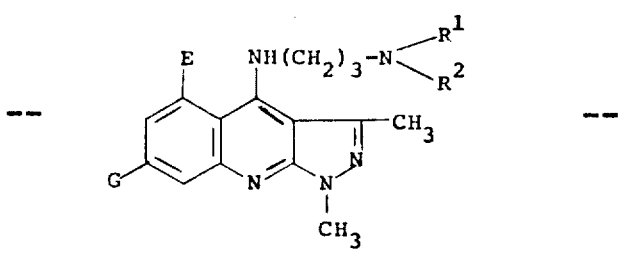

Signed and Sealed this

Ninth Day of May 1978

[SEAL]

Attest:

RUTH C. MASON
Attesting Officer

LUTRELLE F. PARKER
Acting Commissioner of Patents and Trademarks